(12) United States Patent
Streeter

(10) Patent No.: US 6,214,035 B1
(45) Date of Patent: Apr. 10, 2001

(54) METHOD FOR IMPROVING CARDIAC MICROCIRCULATION

(76) Inventor: Jackson Streeter, 3250 Marthiam Ave., Reno, NV (US) 89509

( * ) Notice: Subject to any disclaimer, the term of this patent is extended or adjusted under 35 U.S.C. 154(b) by 0 days.

(21) Appl. No.: 09/343,636

(22) Filed: Jun. 30, 1999

Related U.S. Application Data

(60) Provisional application No. 60/125,691, filed on Mar. 23, 1999.

(51) Int. Cl.$^7$ ................................................. A61N 7/00
(52) U.S. Cl. ............................... 607/89; 606/3; 128/898
(58) Field of Search ................................ 607/89, 92, 93, 607/88; 606/2, 3, 10–14, 15; 604/20, 21; 128/898

(56) References Cited

U.S. PATENT DOCUMENTS

| | | |
|---|---|---|
| 4,930,504 | 6/1990 | Diamantopoulos et al. . |
| 5,445,146 | 8/1995 | Bellinger . |
| 5,464,436 * | 11/1995 | Smith ..................................... 607/89 |
| 5,640,978 | 6/1997 | Wong . |
| 5,755,752 * | 5/1998 | Segal ....................................... 607/89 |
| 5,843,073 | 12/1998 | Sinofsky . |
| 5,989,245 * | 11/1999 | Prescott ................................. 607/89 |
| 6,063,108 | 5/2000 | Salansky et al. . |

OTHER PUBLICATIONS

Agov, B S, et al, "On the mechanism of therapeutic action of helium–neon laser in ischemic heart disease", KLIN MED (Mosc), pp. 102–105, 1985.*

Olesin Al et al, "Laser irradiation of venous blood for prevention of reperfusion syndrome in myocardial infarction", Patologicheskaia fizologiia, pp 20–23, 1992.*

"Lasers In Orthopedic Surgery—Laser Therapy: Scientific Basis and Clinical Role", Jeffrey R. Basford, M.D., Ph.D., May 1993, vol. 16, No. 5, pp. 541–547.

"The Photobiological Basis of Low Level Laser Radiation Therapy", Photobiological Basis of LLLT, Kendric C. Smith, pp. 1–7.

"The Efficacy of Laser Therapy for Musculoskeletal and Skin Disorders: A Criteria–Based Meta–analysis of Randomized Clinical Trials", Physical Therapy/vol. 72, No. 7/Jul. 1992, pp. 483/13–491/21.

"Is Laser Therapy Overtaking Ultrasound?" http://www.laser.uk.com/laser, Therapy vs. ultrasoun.html, dated Feb. 20, 1999.

"Laser Therapy Introduction" http://laser.uk.com/physio.html, Mar. 4, 1999, 12 pgs.

"The use of low power lasers in sports medicine", G.A. Gordon, Clinical Sports Medicine 2, 53–61 (1990).

Low Level Laser Therapy—Clinical Practice and Scientific Background, Jan Turner and Lars Hode, Prima Books in Sweden AB 1999, pp. 1–9; 45–58; 59–109; 113–116; 118; 132–134; and 151–156.

Product List, Thor, lllt, LLLT, Low Level Laser Therapy, Laz., http://www.thorlaser.com/prodlist/index.html, Oct. 6, 1999, pp. 1–4.

(List continued on next page.)

*Primary Examiner*—Michael Peffley
(74) *Attorney, Agent, or Firm*—Armstrong Teasdale LLP

(57) ABSTRACT

A method for improving cardiac microcirculation using low level laser therapy. After a cardiac procedure, a therapist or surgeon maintains contact between a laser probe and a region of myocardium, and applies laser energy with the probe directly to the myocardium, the laser energy having a wavelength of about 630 nm to about 904 nm, with laser apparatus having a mean power output of about 100 mW to about 500 mW, at a dosage of about 1 joule/point to about 10 joules/point. Treatment times, total dosage, and number of treatment points are determined by the therapist trained in LLLT. The method is used immediately post-procedure after cardiac surgeries such as coronary bypass and angioplasty.

10 Claims, 3 Drawing Sheets

OTHER PUBLICATIONS

Specifications, Thor, lllt, LLLT, Low Level Laser Therapy, low level laser therapy, http://www.thorlaser.com/specs/, Oct. 6, 1999, pp. 1–2.

100mW, Thor, lllt, LLLt, Low Level Laser Therapy, low level laser therapy, Lazer, Thorl., http://www.thorlaser.com/specs/100m W.html, Oct. 6, 1999, p. 1.

200mW, Thor, lllt, LLLT, Low Level Laser Therapy, low level laser therapy, Lazer, Thorl., http://www.thorlaser.com/specs/200m W.html, Oct. 6, 1999, p. 1.

500mW, Thor, lllt, LLLT, Low Level Laser Therapy, low level laser therapy, Lazer, Thorl., http://www.thorlaser.com/specs/500m W.html, Oct. 6, 1999, p. 1.

200mW, Thor, lllt, LLLT, Low Level Laser Therapy, low level laser therapy, Lazer, Thorl., http://www.thorlaser.com/specs/200m W650nm.html, Oct. 6, 1999, p. 1.

680nm Probe, Thor, lllt, LLLT, Low Level Laser Therapy, low level laser therapy, Lazer., http://www.thorlaser.com/specs/680.html, Oct. 6, 1999, p.1.

* cited by examiner

METHOD FOR IMPROVING CARDIAC MICROCIRCULATION

CROSS-REFERENCE TO RELATED APPLICATIONS

This application claims the benefit of U.S. provisional application No. 60/125,691 filed Mar. 23, 1999.

BACKGROUND OF THE INVENTION

This invention relates generally to laser apparatus and more particularly, to low level laser therapy apparatus.

High energy laser radiation is now well-accepted as a surgical tool for cutting, cauterizing and ablating biological tissue. High energy lasers are routinely used to vaporize superficial skin lesions, to make superficial incisions such as those required for plastic surgery, and to make deep cuts required for major surgical operations. Such lasers accomplish their results thermally, by heating the tissue.

Less well-known is that low levels of laser energy have a non-thermal, biostimulative effect on biological tissues. The therapeutic application of low level laser energy, frequently known as low level laser therapy (LLLT), produces beneficial clinical effects in the treatment of musculoskeletal, neurological and soft tissue conditions. LLLT is non-invasive and avoids the potential side effects of drug therapy. More specifically, LLLT delivers photons to targeted tissue, penetrating the layers of skin to reach internal tissues to produce a specific, nonthermal photochemical effect at the cellular level. Jeffrey R. Basford, *Laser Therapy: Scientific Basis and Clinical Role*, ORTHOPEDICS, May 1993, at 541. More specifically, one known effect of LLLT is to enhance microcirculation of both blood and lymph. JAN TUNER & LARS HODE, LOW LEVEL LASER THERAPY: CLINICAL PRACTICE AND SCIENTIFIC BACKGROUND 133 (1999).

Currently, the post-surgical recovery of cardiac patients is frequently complicated by reperfusion injury. Reperfusion injury results when myocardium the cardiac procedure. Reperfusion injury results when myocardium which has been rendered hypoxic due to disease is suddenly re-exposed to a healthy supply of oxygenated blood. Under such conditions, endothelial cells activate to release noxious inflammatory products such as leukocyte adhesive molecules, procoagulation factors and vasoconstrictive agents. These products of inflammation cause tissue local tissue damage, thus producing poorer patient outcomes post-surgery. No known methods currently exist to address the problem by directly enhancing microcirculation of the cardiac muscle. Because of the enhancing effect of LLLT on microcirculation, LLLT is likely to aid in the prevention of reperfusion injury by improving the delivery of oxygen, clearing noxious inflammatory products and promoting the healing process.

It would therefore be desirable to provide an LLLT method for reducing the risk of reperfusion injury after cardiac surgical procedures. It would also be desirable to provide such a method which is easily used in conjunction with cardiac surgery. It would also be desirable to provide such a method which is relatively inexpensive to implement and convenient to use.

BRIEF SUMMARY OF THE INVENTION

These and other objects may be attained by a method for improving cardiac microcirculation which in one embodiment includes the step of applying LLLT to areas of, and areas surrounding, ischemic myocardium after cardiac surgery. The application of LLLT increases local myocardial microcirculation and thus reduces the risk of reperfusion injury. In one embodiment, the method employs LLLT apparatus having a mean power output of about 100 mW to about 500 mW, and emitting laser energy at a wavelength in the visible to near-infrared range of about 630 nm to about 904 nm. Dosages per treatment point are from about 1 joule/point to about 10 joules/point, where a point is defined as a spot having a diameter of about 1 cm.

The method is practiced immediately post-procedurally, before closing the surgical incision. To practice the method, an LLLT trained therapist, such as a clinician or physiotherapist, first determines a dosage within the above range, based on the size of the region of ischemic myocardium, the severity of ischemia, and the tissue response to LLLT. The therapist or surgeon then uses a sterilized, handheld laser probe of the LLLT apparatus to apply adequate pressure to maintain contact between the myocardium at treatment points in and around the region of ischemia, and the probe at the point where the probe emits the laser energy. The LLLT apparatus is energized and low levels of laser energy are applied to a treatment point for a treatment time determined by the therapist, or automatically by the LLLT apparatus. Total energy dose, number and location of treatment points, and number of treatments are determined by the treating physician.

Thus, the LLLT method provides a method for the prevention of cardiac reperfusion injury. In addition, the LLLT method is noninvasive, and simple to practice. Further, the LLLT method is relatively inexpensive to implement and convenient to use in conjunction with a range of cardiac surgeries, including coronary bypass surgeries and angioplasty.

DETAILED DESCRIPTION OF THE INVENTION

Figure 1:
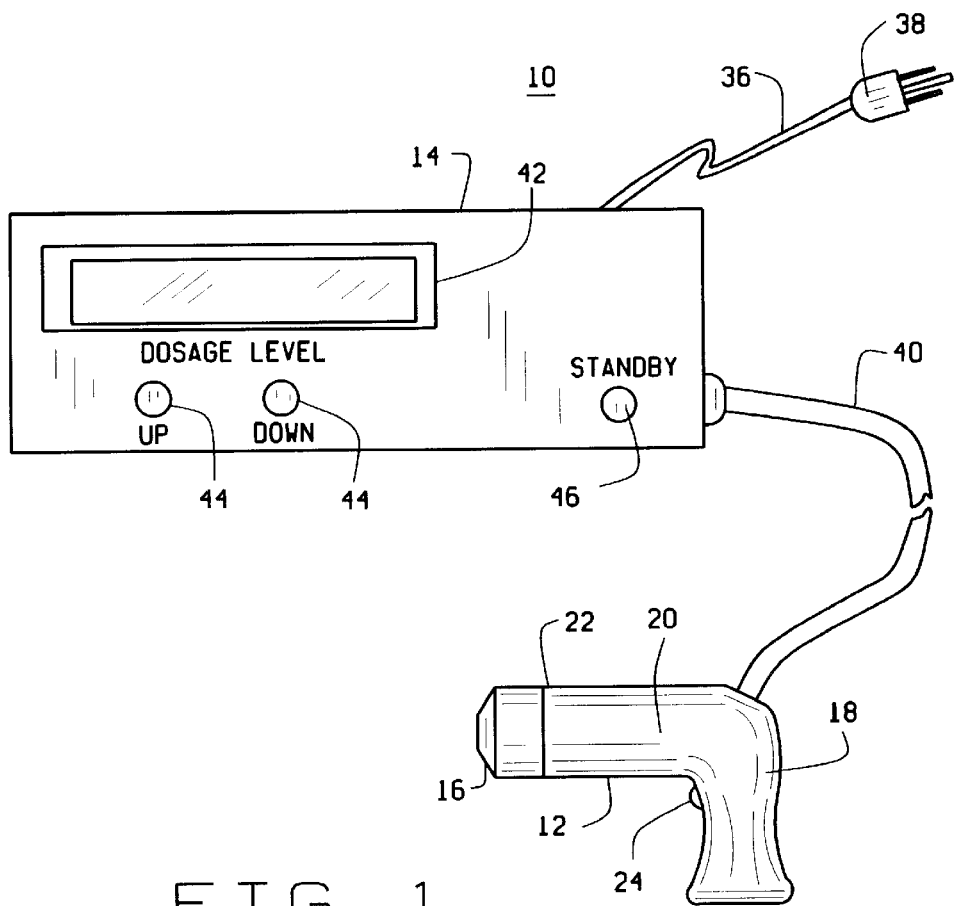
FIG. 1 is a schematic illustration of an LLLT apparatus.

FIG. 1 is a schematic illustration of an LLLT apparatus 10. LLLT apparatus 10 includes a handheld laser probe 12 coupled to a control unit 14. Probe 12 includes a probe head 16 in which laser diodes (not shown in FIG. 1) are mounted. In an exemplary embodiment, four 30 mW laser diodes are mounted in head 16 and angled so that laser beams emitted from the diodes intersect at a short distance away from the head, thus producing a combined mean power output of 120 mW at the point of intersection as described in more detail below. In one embodiment, probe 12 includes a handle portion 18 extending from barrel portion 20 in a substantially pistol-shaped configuration. Head 16 is at a distal end 22 of barrel portion 20. Handle portion 18 and barrel portion 20 are fabricated, for example, from a molded plastic material.

A switch button or trigger 24 is located on handle portion 18. The precise shape of probe 12 is varied among different ergonomic configurations to make repeated and prolonged use of probe 12 more comfortable. For example, in one embodiment handle portion 18 is molded with indentations forming a grip. In an alternative embodiment, probe 12 is a computer mouse-like element having a shape especially suitable for grasping from above, wherein the laser diodes are mounted on a bottom surface and button 24 is located in a position on the mouse-like element which is easily reached with, for example, the index finger. In another alternative embodiment, probe 12 has an elongate, penlight-like shape having two ends, with the laser diode or diodes mounted at one end and button 24 located in a position easily reached with an index finger when probe 12 is grasped as one would typically grasp a pencil.

To limit laser energy within a predetermined range, apparatus 10 includes control unit 14 which includes a box housing circuitry for controlling the operation of apparatus 10. An AC power cord 36 with a grounded plug 38 allows unit 14 to be plugged into a conventional electrical outlet. A second power cord 40 couples probe 12 to control unit 14. In an exemplary embodiment, unit 14 includes a display 42, such as an LED readout, for displaying a pre-selected laser energy dosage level in joules/point, a circuit board (not shown) including a control circuit, a microprocessor (not shown) linked to the control circuit and storing in memory the preselected dosage level, and at least one dosage selection element 44 such as a switch, knob or the like, linked to the control circuit for pre-selecting the dosage level. Generally, the control circuit functions to control the delivery of power to the laser diodes according to a predetermined dosage as selected using dosage selection element 44. In one embodiment as shown in FIG. 1, the dosage selection element 44 is a pair of buttons, with an "Up" button for increasing the dosage, and a "Down" button for decreasing the dosage. In an alternative embodiment, the dosage selection element is a single potentiometer, dial or the like for dialing in the preselected dosage. To limit laser energy dosages within a range, apparatus 10 includes control unit 14 which is a box generally housing circuitry for controlling the operation of apparatus 10. An AC power cord 36 with a grounded plug 38 allows unit 14 to be plugged into a conventional electrical outlet. A second power cord 40 couples probe 12 to control unit 14. In an exemplary embodiment, unit 14 includes a display 42, such as an LED readout, for displaying a pre-selected laser energy dosage level in joules, a circuit board including a control circuit (not shown in FIG. 1), a microprocessor (not shown in FIG. 1) linked to the control circuit and storing in memory the preselected dosage level, and at least one dosage selection element 44 such as a switch, knob or the like, linked to the control circuit for pre-selecting the dosage level. The control circuit is linked to the laser diodes.

Generally, the control circuit functions to control the delivery of power to the laser diodes according to a predetermined dosage within a range, as selected using dosage selection element 44. In one embodiment as shown in FIG. 1, the dosage selection element 44 is a pair of buttons, with an "Up" button for increasing the dosage, and a "Down" button for decreasing the dosage. In an alternative embodiment, the dosage selection element is a single potentiometer, dial or the like for dialing in the preselected dosage. Of course, other implementations of the dosage control element will be obvious to those skilled in the electronics art.

Control unit 14 further includes a locking element 46 for controlling access to, and use of apparatus 10. In an exemplary embodiment as shown in FIG. 1, control unit 14 includes a keyed lock 46 having an OFF position, a STANDBY position and an ON position. The STANDBY and ON positions can only be reached with a matching key (not shown). In the OFF position apparatus 10, including the diodes, is disabled. With the key, and with lock 46 in the STANDBY position, apparatus 10 is enabled for selecting the desired dosage using dosage control element 44. With lock 46 in the ON position and button or trigger 24 depressed, the laser diodes are energized for a period of time calculated by the memory chip to deliver the preselected dosage, the time being dependent on the total power output of the laser diodes.

Figure 2:
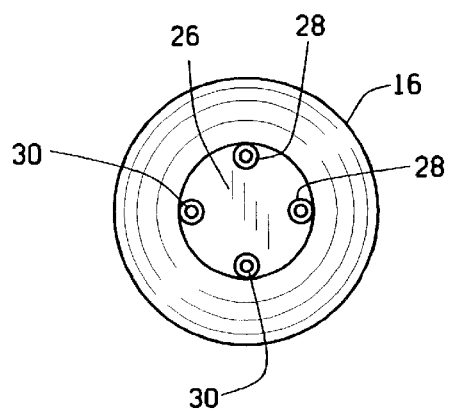
FIG. 2 is a plan view of the low level laser probe head.
Figure 3:
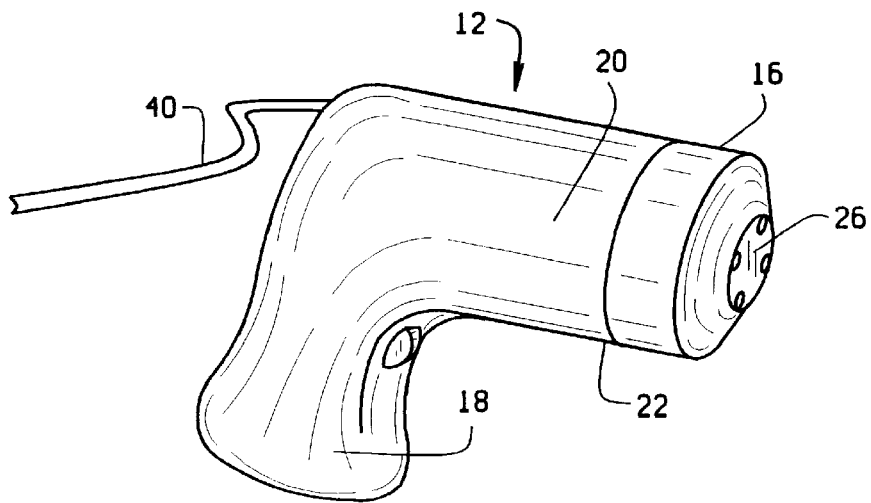
FIG. 3 is a perspective view of a low level laser probe.

FIG. 2 is a plan view of one embodiment of probe head 16. Probe head 16 is substantially cylindrical with a tapered forward end ending in a face 26 having openings 28 from which the laser energy is emitted. FIG. 3 is a perspective view of probe 12 showing more clearly the configuration of probe head 16. Probe head 16 is fabricated from, for example, a metal or plastic material and is coupled to barrel portion distal end 22. In an exemplary embodiment, four 30 mW laser diodes 30 are each mounted in an opening 28 in face 26, and angled so that laser energy beams emitted from each diode substantially overlap or intersect each other at a distance of about 0.5 to about 2.0 cm from face 26 to yield a combined power output of 120 mW in the overlapping area. In one embodiment, diodes 30 are angled in face 26 so that the laser energy beams overlap at a distance of about 1.7 cm from face 26. Generally, diodes 30 are any type which emits biostimulative laser energy, which includes lasers emitting energy at wavelengths between about 630 nm and about 904 nm.

The specific laser diodes chosen depends on the desired wavelength of the emitted laser energy, which depends on a number of factors including cost, as well as the desired level of penetration, and the type of tissue and injury being treated. In addition, some wavelengths appear to be especially suitable for specific applications. For example, low power HeNe lasers emitting at a relatively short wavelength of about 633 nm appear to be especially suited for conditions or injuries requiring lower levels of penetration, such as skin wounds, mucous membranes problems, and eye conditions such as conjunctivitis. However, for most internal tissue injuries amenable to LLLT, a penetration depth of about 2–3 cm is suitable, and is achieved with an intermediate wavelength of about 830 nm, that emitted by GaAlAs laser diodes. In addition to wavelength, the precise number and type of diodes used can be varied, limited only by the requirement that the combined or total mean power output be in the range of about 100 mW to about 500 mW, in pulsed or continuous mode.

Thus, in one embodiment diodes 30 are continuously emitting GaAlAs diodes emitting at a near-infrared wavelength of about 830 nm in a collimated beam. 30 mW GaAlAs diodes are relatively inexpensive, easily commercially obtained, and require only four to provide a mean power output in the range of about 100 mW to about 500 mW. However, higher or lower power GaAlAs diodes, or other biostimulative diodes emitting in the visible to near-infrared wavelength range of about 630 nm to about 904 may be used. For example, in one alternative embodiment, InGaAlP laser diodes are used, emitting at a wavelength of about 630–685 nm. In another alternative embodiment, pulsed GaAs diodes are used, emitting at about 904 nm. In other alternative embodiments, the combined or total power output is varied from about 100 mW to about 500 mW by changing the number and power of diodes used. For example, in one alternative embodiment, a single GaAlAs diode with a power output of 100 mW is used. As explained above, the precise number and type of diodes used is limited only by the requirement that the total power output be in the range of about 100 mW to about 500 mW. However, cost considerations are also a factor in deciding the number and types of diodes employed.

Figure 4:
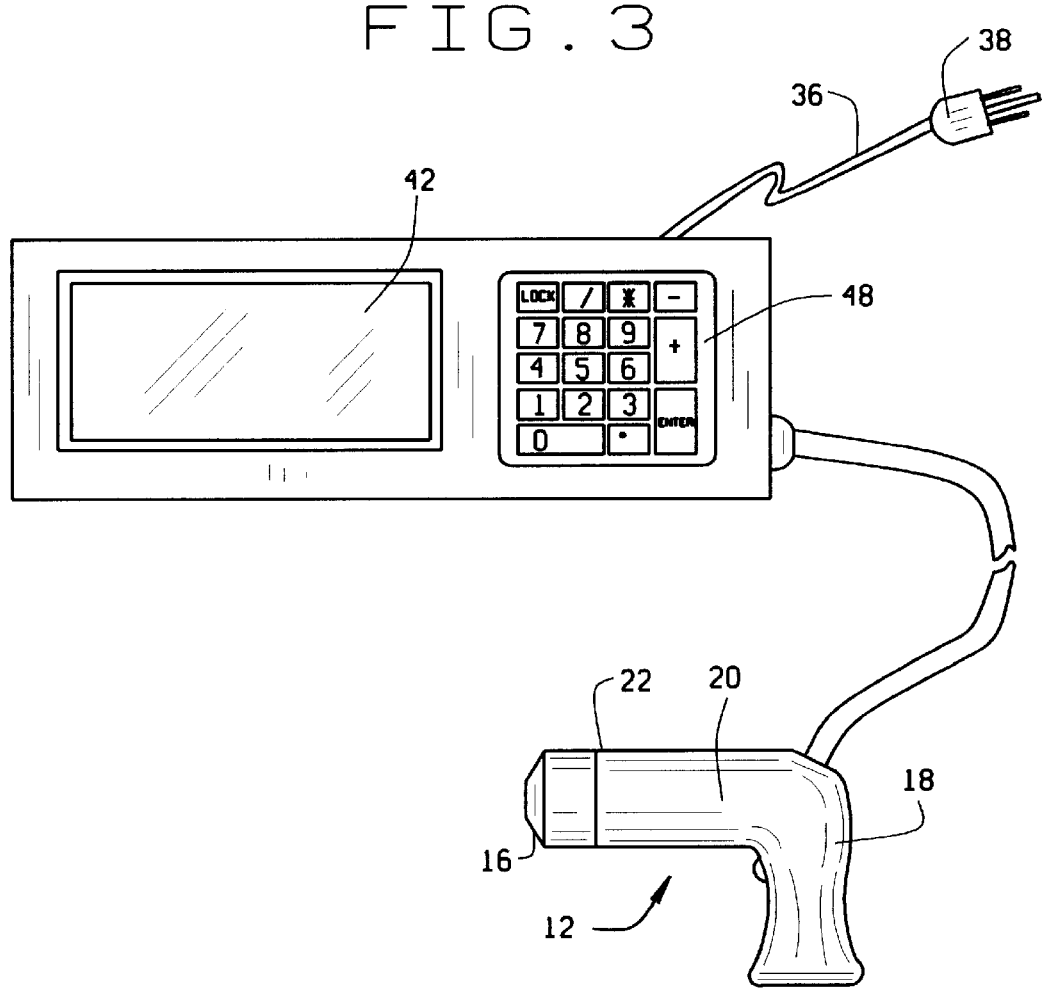
FIG. 4 is a schematic illustration of the LLLT apparatus with a PIN system.

FIG. 4 is a schematic illustration of an alternative embodiment of apparatus 10 in which locking element 46 is implemented with an access code system, such as a personal identification number (PIN) system. The PIN system includes a microprocessor (not shown) included in control unit 14. In this embodiment, control unit 14 includes display 42 and an input device 48 such as a keypad or LCD touch screen for entering data, including PIN's, into the microprocessor. In another alternative embodiment, control unit 14 is communicatively coupled to a compatible computer containing a microprocessor and having its own input device. The microprocessor stores hundreds or thousands of valid multiple-digit PIN's, each associated with a predetermined activation time. The predetermined activation time is a period of minutes sufficient to cover multiple treatments each lasting seconds or minutes. Upon entering a valid PIN, apparatus 10 is enabled to allow dosage selection, and then energizes diodes 30 when button or trigger 24 is depressed. In an alternative embodiment, instead of the PIN system as described above, control unit 14 includes a magnetic card reader for reading a card such as a credit card having a magnetically encoded authorization number for enabling apparatus 10.

As described above, each PIN is associated with a predetermined activation time. With each treatment or use lasting a limited period of seconds or minutes under a given PIN, the microprocessor is programmed to subtract the duration of use, or treatment time, from the activation time remaining on the given PIN. In one embodiment, the treatment time is calculated as the number of seconds or minutes during which diodes 30 are energized. Thus, microprocessor is programmed to keep account of the activation time remaining with each successive use of apparatus 10. For example, in one embodiment each PIN is associated with a total activation time of 100 minutes. With an average treatment time of 10 minutes per treatment, one PIN is used for a total of 10 treatments. Of course, the total number of minutes associated with a single PIN can be varied, as can the use of that time by the PIN holder. In one embodiment, the microprocessor is further programmed to issue a warning displayed on display 42 when a certain limited number of minutes remains in the activation time. For example, the microprocessor is programmed to issue a warning when 10 minutes remains of the total activation time on a given PIN. Of course, the time limit for issuing the warning can be varied.

In one embodiment, valid PIN's are provided via a computer network such as the Internet or Web so that a user of apparatus 10 can purchase activation time electronically. For example, a Web site on a server maintained by the manufacturer or seller of apparatus 10 is linked to a database which stores profile information on each user. A new user first registers with the Web site via a remote computer which is linked to the Web, providing profile information such as name, institution, billing information, and the like. When the profile information has been provided, or accessed from the database after being previously entered, and the user billed for the activation time, a valid PIN number for a predetermined activation time is provided to the user, for example by an automatic e-mail communication to the user, or through a separate Web page. The user then uses the PIN for LLLT treatment until the activation time is exhausted. If desired by the user, additional activation time is purchased in like manner and added, using a separate authorization code, to a previously used PIN so that the user does not need to repeatedly change his or her PIN. Of course, the electronic purchasing system is easily varied to use a magnetically encoded card as described above.

Figure 5:
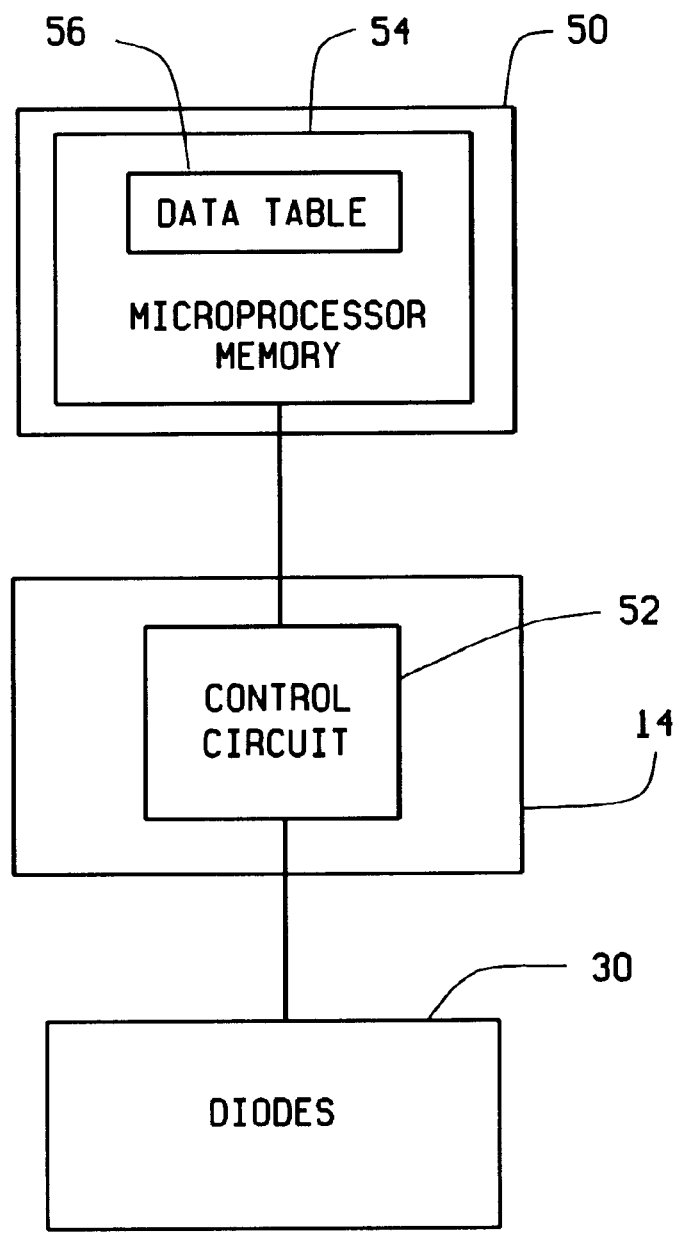
FIG. 5 is a block diagram of the LLLT apparatus.

FIG. 5 is a block diagram of apparatus 10, showing microprocessor 50 coupled to control circuit 52. In one embodiment, microprocessor 50 is programmed to store patient data information for individual patients, so that the user can easily monitor previous LLLT dosages and patient progress. For example, the microprocessor has an on-board memory 54 for storing patient information. In one embodiment, a data table 56 is stored in the microprocessor memory and includes an identifying code for each previous visit (for example the date), and the associated dosage(s), treatment times, codes for treatment locations, and other treatment information from previous treatments. In one embodiment, the patent data information includes a code for specifying the level and location of the patient's pain on each previous visit.

Apparatus 10 is used for treating a variety of tissue injuries, including musculoskeletal injuries, bone fractures, and spinal cord transections, and for improving local microcirculation, particularly cardiac microcirculation. Generally, a dosage of laser energy from about 1 joule/point to about 10 joules/point is chosen by a clinician based on the clinician's experience and training as well as the individual patient's previously demonstrated response to LLLT. The clinician, or a trained technician, accesses apparatus 10 with a key, PIN, or with a password for accessing a software control package as described above. The select dosage is dialed or otherwise input into control unit 14. With apparatus 10 enabled for the selected dosage, the clinician or technician applies face 26 of probe 12 to a point on the patient's skin surface over or near the internal tissue to be treated, applying enough pressure with face 26 at the skin surface so that the skin is slightly blanched. This step clears blood from the path of the laser energy to decrease absorption of the laser energy by the blood, thus allowing the greatest depth of penetration through the dermal structures to the internal injury. Button 24 is depressed and laser diodes 30 energized so that laser energy is applied, point by point, across the skin surface over the site or region of injury. If necessary, the treatment is repeated at intervals of about 1 to about 3 or 4 days. Number of treatment points and separation of treatment points, as well as the number of repeat treatments, varies with the location and type if injury, as well as the individual patient's response to LLLT.

More specifically, to improve cardiac microcirculation in regions of ischemic myocardium after a cardiac procedure, such as a bypass procedure, LLLT is applied with apparatus 10 immediately after the procedure and before closing the surgical incision. Thus, the surgeon still has direct access to the myocardium. Apparatus 10, or at least probe 12, is sterilized before the procedure. An LLLT trained therapist, such as the surgeon, another clinician or a physiotherapist, first determines a dosage within the range of about 1 joule/point to about 10 joules/point, where one point is a spot having a diameter of about 1 cm. Dosages are based on the size of the myocardium, type and severity of the injury, and the tissue response to LLLT. The surgeon then uses the sterile handheld probe 12 to apply adequate pressure with probe head 16 to maintain contact with, and treat, a series of treatment points in a region of ischemic myocardium to be treated. In one embodiment, probe head 16 is successively held in contact with, and used to treat, a series of points along the periphery of the region of ischemia. More specifically, in one embodiment of the method as practiced post-bypass procedure, probe head 16 is used to apply low level laser energy to ischemic myocardium distal to bypass grafts. Generally, at each treatment point, apparatus 10 is energized and low levels of laser energy are applied at the point for a treatment time determined by the therapist, or automatically by the LLLT apparatus. Total energy dose, number and location of treatment points, and number of treatments are determined by the treating physician.

The LLLT methods provide a new approach to reducing the risk of reperfusion injury after cardiac procedures. The LLLT methods provide a way of directly enhancing local cardiac microcirculation, thus improving the local delivery of oxygen, clearing noxious inflammatory products and preventing tissue injury due to inflammation. Further, the LLLT methods are simple, relatively inexpensive, avoid the use of drug therapy, and are easily practiced post-operatively with respect to common cardiac procedures.

From the embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method of using low level laser therapy, said method comprising preventing reperfusion injury in myocardium after a cardiac surgical procedure by applying a low level of laser energy directly to the region of ischemic myocardium before closing a surgical incision for the cardiac surgical procedure.

2. A method in accordance with claim 1 wherein preventing reperfusion injury in myocardium after a cardiac surgical procedure by applying a low level of laser energy directly to the region of ischemic myocardium comprises applying laser energy having a wavelength of about 630 nm to about 904 nm, with a handheld laser apparatus having a mean power output of about 100 mW t about 500 mW.

3. A method in accordance with claim 1 wherein preventing reperfusion injury in myocardium after a cardiac surgical procedure by applying a low level of laser energy directly to the region of ischemic myocardium comprises applying the laser energy at a dosage of about 1 joule/point to about 10 joules/point.

4. A method of preventing reperfusion injury in cardiac muscle after a cardiac surgical procedure, said method comprising applying laser energy directly to an area of ischemic myocardium before closing the surgical incision, the laser energy having a wavelength in the visible to near-infrared range, for a period sufficient to deliver a dosage of the laser energy between about 1 joule/point and about 10 joules/point.

5. A method in accordance with claim 4 wherein applying laser energy directly to an area of ischemic myocardium comprises maintaining contact between a laser source emitting the laser energy and the area of ischemic myocardium.

6. A method for preventing reperfusion injury in myocardium after a cardiac surgical procedure, said method comprising before closing a surgical incision for the cardiac surgical procedure, applying laser energy having a wavelength in the visible to near-infrared range to at least one treatment point in a region of ischemic myocardium using a low level laser apparatus comprising a handheld laser probe including a plurality of laser diodes sufficient to provide the laser energy at a mean power output of about 100 mW to about 500 mW in the visible to near-infrared wavelength range.

7. A method in accordance with claim 6 wherein applying laser energy to at least one treatment point in a region of ischemic myocardium comprises the step of applying the laser energy at a dosage of about 1 joule/point to about 10 joules/point.

8. A method in accordance with claim 6 wherein applying laser energy to a region of ischemic myocardium comprises the step of applying the laser energy with a laser source in contact with the region of ischemic myocardium.

9. A method in accordance with claim 6 wherein the cardiac surgical procedure is a bypass procedure and wherein applying the laser energy to at least one treatment point in a region of ischemic myocardium using the low level laser apparatus comprises applying low level laser energy to ischemic myocardium distal to bypass grafts.

10. A method in accordance with claim 6 wherein applying the laser energy to at least one treatment point in a region of ischemic myocardium using the low level laser apparatus comprises successively applying the laser energy with the handheld laser probe to a plurality of treatment points along the periphery of the region of ischemic myocardium.

* * * * *